US011406251B2

(12) United States Patent
Maurice

(10) Patent No.: US 11,406,251 B2
(45) Date of Patent: Aug. 9, 2022

(54) HYBRID APPARATUS FOR FLUID SUPPLY FOR ENDOSCOPIC IRRIGATION AND LENS CLEANING

(71) Applicant: ERBE-USA, Inc., Marietta, GA (US)

(72) Inventor: Daniel G. Maurice, Monument Beach, MA (US)

(73) Assignee: ERBE-USA, Inc., Marietta, GA (US)

( * ) Notice: Subject to any disclaimer, the term of this patent is extended or adjusted under 35 U.S.C. 154(b) by 0 days.

(21) Appl. No.: 17/401,264

(22) Filed: Aug. 12, 2021

(65) Prior Publication Data

US 2022/0031152 A1 Feb. 3, 2022

Related U.S. Application Data

(60) Continuation of application No. 17/162,135, filed on Jan. 29, 2021, now abandoned, which is a continuation of application No. 16/130,440, filed on Sep. 13, 2018, now Pat. No. 10,952,595, which is a continuation of application No. 15/610,501, filed on May 31, 2017, now Pat. No. 10,098,525, which is a continuation of application No. 14/832,567, filed on Aug. 21, 2015, now Pat. No. 10,111,578, which is a
(Continued)

(51) Int. Cl.
*A61B 1/00* (2006.01)
*A61B 1/31* (2006.01)
*A61B 1/015* (2006.01)
*A61B 1/12* (2006.01)

(52) U.S. Cl.
CPC .......... *A61B 1/015* (2013.01); *A61B 1/00128* (2013.01); *A61B 1/00142* (2013.01); *A61B 1/126* (2013.01); *A61B 1/127* (2013.01); *A61B 1/31* (2013.01)

(58) Field of Classification Search
CPC . A61B 1/015; A61B 1/00128; A61B 1/00142; A61B 1/126; A61B 1/127; A61B 1/31
See application file for complete search history.

(56) References Cited

U.S. PATENT DOCUMENTS

| 3,903,877 A | 9/1975 | Terada |
| D239,025 S | 3/1976 | D'Alo |
(Continued)

FOREIGN PATENT DOCUMENTS

| CN | 101507597 A | 8/2009 |
| EP | 0082950 A2 | 7/1983 |
(Continued)

OTHER PUBLICATIONS

Extended European Search Report for European Patent Application No. 11008045.4, dated Jun. 19, 2012, 7 pages.
(Continued)

*Primary Examiner* — Timothy J Neal
*Assistant Examiner* — William B Chou
(74) *Attorney, Agent, or Firm* — Cooley LLP

(57) ABSTRACT

A hybrid apparatus for delivery of fluid in connection with endoscopic irrigation and lens cleaning including a connector which is adaptable to a flexible or rigid container, a connector arranged at the end thereof and connected via a tubing supply to a fluid, air and or gas source and to an endoscope during a procedure.

24 Claims, 9 Drawing Sheets

Related U.S. Application Data continuation of application No. 14/496,309, filed on Sep. 25, 2014, now Pat. No. 9,144,374, which is a division of application No. 13/230,576, filed on Sep. 12, 2011, now Pat. No. 8,870,756.

(60) Provisional application No. 61/391,277, filed on Oct. 8, 2010.

(56) References Cited

U.S. PATENT DOCUMENTS

| | | |
|---|---|---|
| D245,921 S | 9/1977 | Beran |
| 4,253,448 A | 3/1981 | Terada |
| 4,301,799 A | 11/1981 | Pope, Jr. et al. |
| 4,311,134 A | 1/1982 | Mitsui et al. |
| 4,325,362 A | 4/1982 | Ouchi et al. |
| D266,790 S | 11/1982 | McCord |
| D271,618 S | 11/1983 | Nishigaki |
| 4,489,712 A | 12/1984 | Ohshima |
| 4,542,130 A | 9/1985 | Weissmuller et al. |
| 4,548,197 A | 10/1985 | Kinoshita |
| 4,552,130 A | 11/1985 | Kinoshita |
| 4,667,655 A | 5/1987 | Ogiu et al. |
| 4,760,838 A | 8/1988 | Fukuda |
| D300,361 S | 3/1989 | Tokarz |
| 4,828,295 A | 5/1989 | Plaquin et al. |
| 4,844,052 A | 7/1989 | Iwakoshi et al. |
| D302,729 S | 8/1989 | Stephens et al. |
| 5,027,791 A | 7/1991 | Takahashi |
| D325,023 S | 3/1992 | Lee et al. |
| 5,133,336 A | 7/1992 | Savitt et al. |
| 5,151,101 A | 9/1992 | Grossi et al. |
| 5,152,746 A | 10/1992 | Atkinson et al. |
| 5,191,878 A | 3/1993 | Iida et al. |
| D340,316 S | 10/1993 | Zdrok |
| 5,297,537 A | 3/1994 | Savitt et al. |
| 5,328,478 A | 7/1994 | McVay |
| 5,402,770 A | 4/1995 | Iida et al. |
| 5,437,654 A | 8/1995 | McVay |
| 5,470,324 A | 11/1995 | Cook et al. |
| D366,863 S | 2/1996 | Lee |
| D371,513 S | 7/1996 | Scudder et al. |
| 5,536,254 A | 7/1996 | McVay |
| 5,630,795 A | 5/1997 | Kuramoto et al. |
| 5,707,351 A | 1/1998 | Dorsey, III |
| 5,807,313 A | 9/1998 | Delk et al. |
| 5,830,128 A | 11/1998 | Tanaka |
| 6,027,499 A | 2/2000 | Johnston et al. |
| D435,513 S | 12/2000 | Cheng |
| 6,210,322 B1 | 4/2001 | Byrne |
| 6,287,848 B1 | 9/2001 | Hamzeh et al. |
| 6,485,412 B1 | 11/2002 | Byrne |
| 6,499,615 B1 | 12/2002 | Szieff et al. |
| 6,523,711 B1 | 2/2003 | Hughes et al. |
| D472,630 S | 4/2003 | Douglas et al. |
| 6,764,442 B2 | 7/2004 | Ota et al. |
| D496,998 S | 10/2004 | Pajunk et al. |
| 6,855,109 B2 | 2/2005 | Obata et al. |
| D530,669 S | 10/2006 | Shing |
| 7,204,382 B2 | 4/2007 | Cezeaux |
| D543,509 S | 5/2007 | Victor |
| 7,276,023 B2 | 10/2007 | Annecke |
| 7,462,068 B2 | 12/2008 | Amidon |
| D612,496 S | 3/2010 | Bennison |
| 7,678,044 B2 | 3/2010 | Fujikura |
| D613,403 S | 4/2010 | Poll et al. |
| D624,181 S | 9/2010 | Harata et al. |
| D627,039 S | 11/2010 | Yu |
| D636,079 S | 4/2011 | Leypold et al. |
| D652,923 S | 1/2012 | Kennedy et al. |
| D657,870 S | 4/2012 | Becker |
| 8,152,790 B2 | 4/2012 | Lopez et al. |
| D661,257 S | 6/2012 | Natoli |
| 8,206,375 B2 | 6/2012 | Snow |
| 8,231,574 B2 | 7/2012 | Haack et al. |
| 8,308,726 B2 | 11/2012 | Kumar et al. |
| 8,333,690 B2 | 12/2012 | Ikeda |
| D676,544 S | 2/2013 | Blocher |
| D678,521 S | 3/2013 | Mort et al. |
| 8,435,172 B2 | 5/2013 | Banik et al. |
| 8,485,818 B2 | 7/2013 | Boutoussov et al. |
| 8,535,219 B2 | 9/2013 | Smith et al. |
| D693,465 S | 11/2013 | Koehler et al. |
| 8,764,642 B2 | 7/2014 | Bendele et al. |
| D712,014 S | 8/2014 | Guest |
| 8,870,756 B2 | 10/2014 | Maurice |
| D717,432 S | 11/2014 | Leroy et al. |
| D719,650 S | 12/2014 | Arinobe et al. |
| D724,703 S | 3/2015 | Downs |
| D732,664 S | 6/2015 | Woehr et al. |
| D739,527 S | 9/2015 | Chauvette |
| 9,144,374 B2 | 9/2015 | Maurice, Jr. |
| D741,805 S | 10/2015 | Davidson, Jr. |
| D742,508 S | 11/2015 | Row et al. |
| D749,212 S | 2/2016 | Chauvette |
| D749,213 S | 2/2016 | Chauvette |
| D750,235 S | 2/2016 | Maurice |
| D750,236 S | 2/2016 | Maurice |
| 9,307,890 B2 | 4/2016 | Ouchi |
| 9,408,523 B2 | 8/2016 | Grudo et al. |
| D777,112 S | 1/2017 | Watkins |
| D785,790 S | 5/2017 | Lewis et al. |
| D791,310 S | 7/2017 | Maurice |
| D791,939 S | 7/2017 | Turturro et al. |
| D791,940 S | 7/2017 | Maurice |
| D793,551 S | 8/2017 | Nelson |
| D796,035 S | 8/2017 | Turturro et al. |
| D797,927 S | 9/2017 | Schuessler et al. |
| D799,031 S | 10/2017 | Barrett et al. |
| D805,637 S | 12/2017 | Bureau |
| D816,211 S | 4/2018 | Guala |
| D820,980 S | 6/2018 | Maurice |
| D825,737 S | 8/2018 | Yokoyama |
| D826,400 S | 8/2018 | Nelson |
| D827,130 S | 8/2018 | Penttila |
| 10,052,472 B2 | 8/2018 | Maurice |
| D831,201 S | 10/2018 | Holtz et al. |
| 10,098,525 B2 | 10/2018 | Maurice |
| 10,111,578 B2 | 10/2018 | Maurice |
| D835,266 S | 12/2018 | Maurice |
| D848,602 S | 5/2019 | Yokoyama |
| D867,587 S | 11/2019 | Holtz et al. |
| D867,588 S | 11/2019 | Rogge et al. |
| D867,913 S | 11/2019 | Hietala et al. |
| D912,246 S | 3/2021 | Maurice |
| 10,952,595 B2 | 3/2021 | Maurice |
| 2001/0039370 A1 | 11/2001 | Takahashi et al. |
| 2002/0040181 A1 | 4/2002 | Arai et al. |
| 2002/0092858 A1 | 7/2002 | Bowman |
| 2002/0185379 A1 | 12/2002 | Schrenk et al. |
| 2003/0018238 A1 | 1/2003 | Obata et al. |
| 2003/0045779 A1 | 3/2003 | Ito |
| 2005/0025646 A1 | 2/2005 | Miller et al. |
| 2005/0159702 A1 | 7/2005 | Sekiguchi et al. |
| 2005/0215856 A1 | 9/2005 | Fujikura |
| 2005/0222499 A1 | 10/2005 | Banik et al. |
| 2005/0263480 A1 | 12/2005 | Smolko et al. |
| 2006/0047184 A1 | 3/2006 | Banik et al. |
| 2006/0052665 A1 | 3/2006 | Aizenfeld et al. |
| 2006/0052666 A1 | 3/2006 | Kumar et al. |
| 2006/0229498 A1 | 10/2006 | Kohno |
| 2006/0241348 A1 | 10/2006 | Kohno |
| 2006/0252989 A1 | 11/2006 | Bar-Or et al. |
| 2006/0266423 A1 | 11/2006 | Akiba et al. |
| 2007/0043262 A1 | 2/2007 | Levy et al. |
| 2007/0161970 A1 | 7/2007 | Spohn et al. |
| 2007/0204890 A1 | 9/2007 | Torii |
| 2007/0225566 A1 | 9/2007 | Kawanishi |
| 2007/0238929 A1 | 10/2007 | Aizenfeld et al. |
| 2007/0244363 A1 | 10/2007 | Sano et al. |
| 2007/0255256 A1 | 11/2007 | Fischer, Jr. et al. |
| 2008/0091061 A1 | 4/2008 | Kumar et al. |
| 2008/0125629 A1 | 5/2008 | Banik et al. |
| 2008/0154095 A1 | 6/2008 | Stubkjaer et al. |

(56) References Cited

U.S. PATENT DOCUMENTS

| | | |
|---|---|---|
| 2008/0167527 A1 | 7/2008 | Slenker et al. |
| 2008/0193631 A1 | 8/2008 | Kanamori et al. |
| 2008/0214891 A1 | 9/2008 | Slenker et al. |
| 2009/0023996 A1 | 1/2009 | Fujikura |
| 2009/0032533 A1 | 2/2009 | Kessell et al. |
| 2009/0090398 A1 | 4/2009 | Onishi |
| 2009/0209822 A1 | 8/2009 | Ikeda |
| 2009/0264705 A1 | 10/2009 | Cushner et al. |
| 2009/0306476 A1 | 12/2009 | Banik et al. |
| 2010/0010307 A1 | 1/2010 | Schramm |
| 2010/0094089 A1 | 4/2010 | Litscher et al. |
| 2010/0125164 A1 | 5/2010 | LaBombard |
| 2010/0185139 A1 | 7/2010 | Stearns et al. |
| 2010/0210907 A2 | 8/2010 | Schramm |
| 2010/0256448 A1 | 10/2010 | Smith et al. |
| 2010/0292644 A1 | 11/2010 | Haack et al. |
| 2011/0004065 A2 | 1/2011 | Schramm |
| 2011/0263939 A1 | 10/2011 | Kaye et al. |
| 2012/0088973 A1 | 4/2012 | Morimoto |
| 2012/0088974 A1 | 4/2012 | Maurice |
| 2012/0091092 A1 | 4/2012 | Adams et al. |
| 2012/0095293 A1 | 4/2012 | Bendele et al. |
| 2012/0095391 A1 | 4/2012 | Bendele et al. |
| 2012/0095537 A1 | 4/2012 | Hall et al. |
| 2014/0309496 A1 | 10/2014 | Bendele et al. |
| 2014/0316205 A1 | 10/2014 | Bendele et al. |
| 2015/0141757 A1 | 5/2015 | Maurice, Jr. |
| 2015/0257634 A1 | 9/2015 | Nakade |
| 2015/0374213 A1 | 12/2015 | Maurice, Jr. |
| 2016/0089002 A1 | 3/2016 | Burton et al. |
| 2016/0121095 A1 | 5/2016 | Maurice, Jr. |
| 2017/0265727 A1 | 9/2017 | Maurice |
| 2019/0223701 A1 | 7/2019 | Maurice |
| 2020/0121171 A1* | 4/2020 | Kaye ............... A61B 1/12 |
| 2020/0187756 A1 | 6/2020 | Maurice |

FOREIGN PATENT DOCUMENTS

| | | |
|---|---|---|
| JP | S59151930 A | 8/1984 |
| JP | S62277935 A | 12/1987 |
| JP | H0373101 U | 7/1991 |
| JP | H0753149 B2 | 6/1995 |
| JP | H08106052 A | 4/1996 |
| JP | 2003093334 A | 4/2003 |
| JP | 2003305003 A | 10/2003 |
| JP | 2004202248 A | 7/2004 |
| JP | 2004242877 A | 9/2004 |
| JP | 2009504302 A | 2/2009 |

OTHER PUBLICATIONS

Extended European Search Report for European Patent Application No. 18848761.5, dated Mar. 24, 2021, 9 pages.

GIMA, Adapter Wolf Endoscope, Product Description [online], Retrieved from the Internet: https://www.gimaitaly.com/prodotti.asp?sku=30845&dept_selected=470&dept_id =4701, Retrieved on May 7, 2020, 1 page.

International Search Report and Written Opinion for International Application No. PCT/US2018/047977, dated Oct. 26, 2018, 10 pages.

* cited by examiner

HYBRID APPARATUS FOR FLUID SUPPLY FOR ENDOSCOPIC IRRIGATION AND LENS CLEANING

CROSS-REFERENCE TO RELATED APPLICATION

This application is a continuation of U.S. patent application Ser. No. 17/162,135, filed Jan. 29, 2021, entitled "Hybrid Apparatus For Fluid Supply For Endoscopic Irrigation and Lens Cleaning," which is a continuation of U.S. patent application Ser. No. 16/130,440, filed Sep. 13, 2018, now U.S. Pat. No. 10,952,595, entitled "Hybrid Apparatus For Fluid Supply For Endoscopic Irrigation and Lens Cleaning," which is a continuation of U.S. patent application Ser. No. 15/610,501, filed May 31, 2017, now U.S. Pat. No. 10,098,525, entitled "Hybrid Apparatus For Fluid Supply For Endoscopic Irrigation and Lens Cleaning," which is a continuation of U.S. patent application Ser. No. 14/832,567, filed Aug. 21, 2015, now U.S. Pat. No. 10,111,578, entitled "Hybrid Apparatus For Fluid Supply For Endoscopic Irrigation and Lens Cleaning," which is a continuation of U.S. patent application Ser. No. 14/496,309, filed Sep. 25, 2014, now U.S. Pat. No. 9,144,374, entitled "Hybrid Apparatus For Fluid Supply For Endoscopic Irrigation and Lens Cleaning," which is a divisional of U.S. patent application Ser. No. 13/230,576, filed Sep. 12, 2011, now U.S. Pat. No. 8,870,756, entitled "Hybrid Apparatus For Fluid Supply For Endoscopic Irrigation and Lens Cleaning," which claims priority to and the benefit of U.S. Provisional Patent Application Ser. No. 61/391,277, filed Oct. 8, 2010, entitled "Hybrid Apparatus for Fluid Supply for Endoscopic Irrigation and Lens Cleaning," the disclosures of which are hereby incorporated by reference in their entireties.

BACKGROUND

Embodiments herein generally relate to endoscopic irrigation systems and procedures. More specifically, the embodiments relate to the supply of fluid in conjunction with an endoscope to enable both endoscopic lens cleaning and endoscopic lavage (irrigation) from a single fluid source.

The desire to visualize inside the "living" human body via a light guiding tube instrument dates back to the early 1800's. The next several decades yielded advancements in light guiding tube instruments with the first successful visualization of the inside of a living human stomach by Dr. Rudolph Kussmaul (Germany) in 1868, followed by continued advancements with flexible fiberscopes in the 1960's. Today, many structures once considered beyond the realm of diagnostic evaluation and therapeutic intervention can now be visualized and treated by the endoscopist. For example, without the use of an "open" surgical technique, the endoscopist can provide a diagnostic evaluation and therapeutic intervention of the esophagus, stomach, duodenum, small intestine, biliary and pancreatic system. The diagnosis and treatment of many gastrointestinal (GI) disorders such as foreign body removal, gallstone removal, polyp removal, tissue biopsy, structure dilatation, stent placement (for patency and drainage), bleeding and haemostasis, require visual inspection, access to the inner parts of the gastrointestinal tract, endoscopic lavage (irrigation) and lens cleaning.

Due to the lower morbidity and mortality associated with endoscopic procedures and the increased utility associated with "higher" risk patient populations, endoscopic diagnostic and therapeutic interventions, specifically a colonoscopy, is one of the most widely performed medical procedures in the United States. Tens of millions of colonoscopy procedures are performed annually and are expected to increase in the coming years, resulting in an exponential explosion in operating expenses to an already fragile medical system.

During a routine diagnostic colonoscopy or a more complicated treatment of acute lower gastrointestinal bleeding, it is not uncommon to encounter mucus secretions, stool, and or bleeding which limits the endoscopist's visualization and therapeutic capabilities. To maintain a clear operative field and also acceptable visualization, a typical endoscopic system (e.g., Fujinon, Olympus, or Pentax) provides a way of delivering sterile water at a high flow rate for endoscopic lavage (irrigation) and a way of delivering sterile water at a comparatively low flow rate for optical lens cleaning. To deliver the sterile water at the higher flow rate needed for endoscopic lavage, a mechanical peristaltic pump is typically used to deliver the sterile water from a vented fluid supply, while the sterile water for the lower flow rate lens cleaning function is supplied from a separate pressurized (non-vented) fluid supply.

Traditionally, since the lavage and lens cleaning functions utilize different mechanisms to deliver the sterile water, separate fluid supplies (1,000 ml and 500 ml respectively) are used. The fluid supplies can be reusable bottles that are re-sterilized once every 24 hours. Due to stringent infection control procedures, however, some facilities have decided to use separate disposable fluid systems for both the lavage (irrigation) and lens cleaning functions. While this practice addresses some of the infection control recommendations, the increased financial burden on medical facilities across the country continues to go unaddressed at the precipice of an exponential explosion in the annual number of procedures.

Thus, the need exists for the supply of fluid in conjunction with an endoscope to enable both endoscopic lens cleaning and endoscopic lavage (irrigation) from a single fluid source.

SUMMARY

A hybrid apparatus and methods for fluid supply for endoscopic irrigation and lens cleaning are described herein. In some embodiments, the hybrid apparatus includes a connector (also referred to herein as a "cap") which is adaptable to a flexible or rigid container that defines a chamber configured to contain a fluid. The hybrid apparatus includes a first tube, defining a first lumen therethrough, a second tube, defining a second lumen therethrough, and a third tube, defining a third lumen therethrough. The first tube fluidically couples with the chamber of the fluid source and a gas source such as to provide a gas (e.g., atmospheric air, oxygen, $CO_2$, etc.) to the fluid chamber. The second tube includes a first end and a second end. The first end of the second tube is configured to couple to the endoscope in any suitable manner dictated by the endoscope. The second end of the second tube is received through a first opening in the connector and configured to be disposed within the fluid to transport the fluid from the fluid source to the endoscope for, for example, endoscopic lens cleaning. The third tube includes a first end and a second end. The first end of the third tube is configured to couple to the endoscope and/or a peristaltic pump in any suitable manner dictated by the endoscope and/or peristaltic pump. The second end of the third tube couples to the connector such that at least a portion of the second end is disposed within the fluid and is configured to transport the fluid from the fluid source to the endoscope for endoscopic lavage.

DETAILED DESCRIPTION

Figure 1:
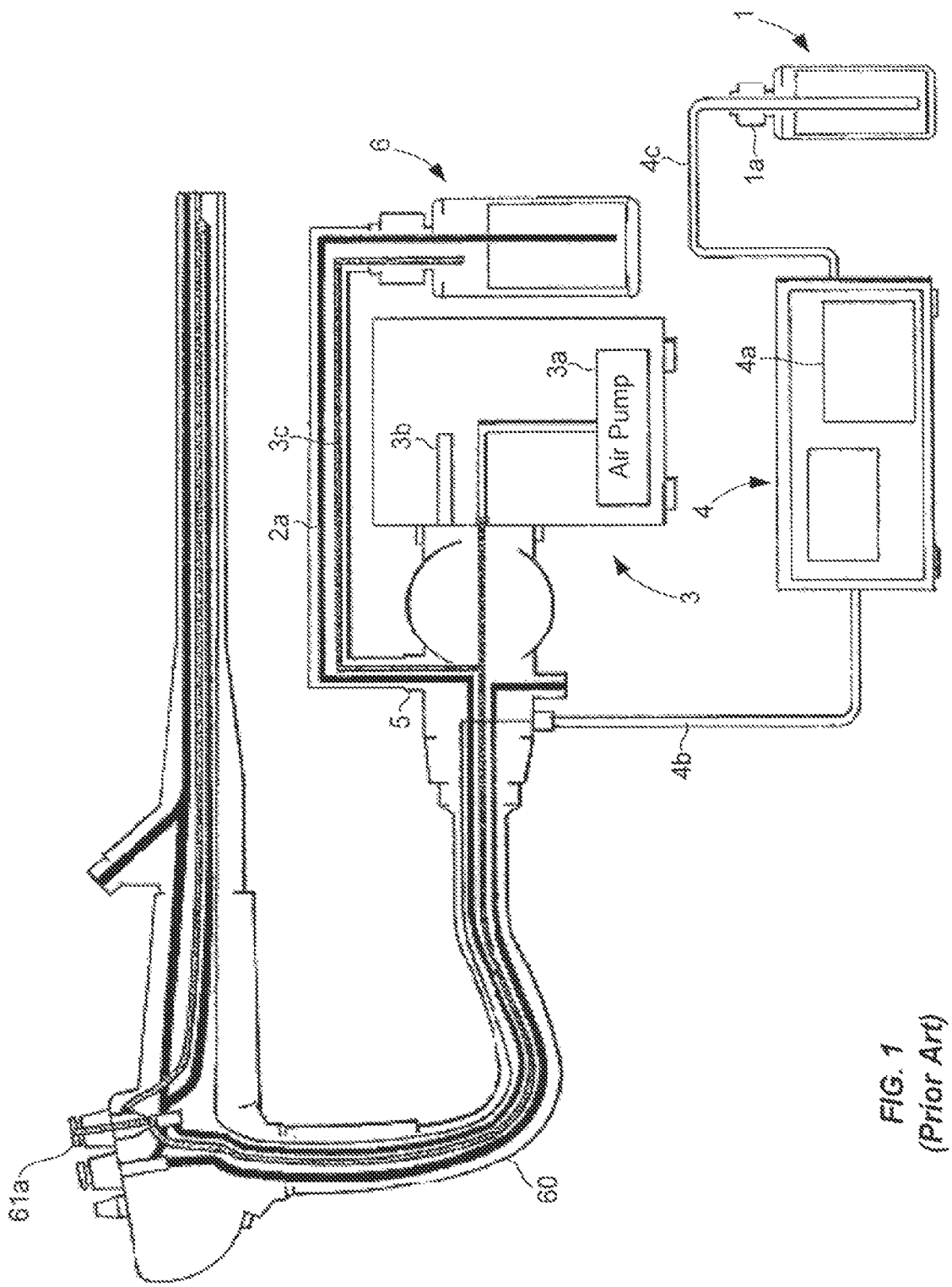
FIG. 1 is a partial cross-sectional schematic illustration of a common endoscopic system.

A hybrid apparatus is disclosed that includes a connector adaptable to a flexible or rigid container that defines a chamber configured to contain a fluid. The hybrid apparatus includes a first tube, defining a first lumen therethrough, a second tube, defining a second lumen therethrough, and a third tube, defining a third lumen therethrough. The first tube fluidically couples with the chamber of the fluid source and a gas source to provide a gas (e.g., air, oxygen, $CO_2$, etc.) to the fluid chamber. The second tube includes a first end and a second end. The first end of the second tube is configured to couple to the endoscope in any suitable manner as appropriate for the particular endoscope. The second end of the second tube is received through a first opening in the connector and configured to be disposed within the fluid, to transport the fluid from the fluid source to the endoscope for endoscopic lens cleaning. The fluid can be any suitable liquid used for endoscopic lens cleaning and/or irrigation. The third tube includes a first end and a second end. The first end of the third tube is configured to couple to the endoscope and/or a peristaltic pump in any suitable manner appropriate for the particular endoscope and/or peristaltic pump. The second end of the third tube couples to the connector such that at least a portion of the second end is disposed within the fluid and is configured to transport the fluid from the fluid source to the endoscope for endoscopic lavage.

In some embodiments, the apparatus is configured to provide fluid from the fluid source in any suitable manner. For example, the second tube conveys the fluid to the endoscope during a first time period and the third tube conveys the fluid to the endoscope during a second time period. The first and second time period can be, for example, at least partially concurrent (i.e., occurring at the same time) or independent. Additionally, the second tube can include at least one valve configured to prevent the flow of fluid within the lumen of the second tube into the chamber of the fluid source. Similarly, the third tube can include at least one valve configured to prevent the flow of fluid from the endoscope and/or an irrigation site proximate to the endoscope into the chamber of the fluid source.

In some embodiments, a hybrid apparatus for delivery of a fluid in connection with endoscopic irrigation and lens cleaning includes a connector which is adaptable to a flexible or rigid container that defines a chamber configured to contain a fluid. The hybrid apparatus includes a first tube, defining a first lumen therethrough, a second tube, defining a second lumen therethrough, and a third tube, defining a third lumen therethrough. The first tube fluidically couples with the chamber of the fluid source and a gas source to provide a gas to the fluid chamber and increase the pressure within the fluid chamber. The second tube includes a first end and a second end. The first end of the second tube is configured to couple to the endoscope in any suitable manner for the particular endoscope. At least a portion of the second tube is configured to be disposed within the lumen defined by the first tube. The second end of the second tube is received through a first opening in the connector and configured to be disposed within the fluid. The second end can include a valve configured to prevent the flow of fluid within the lumen of the second tube into the chamber of the fluid source. The second tube is configured to convey the fluid in response to an increase of pressure in the chamber produced by the gas at a first flow rate and transport the fluid from the fluid source to the endoscope for endoscopic lens cleaning.

In some embodiments, the third tube includes a first end and a second end. The first end of the third tube is configured to couple to the endoscope and/or a peristaltic pump in any suitable manner for the particular endoscope and/or peristaltic pump. The second end of the third tube couples to the connector such that at least a portion of the second end is disposed within the fluid. The third tube is configured to convey the fluid in response to the increase of pressure in the chamber produced by the gas and/or a peristaltic pump and transport the fluid from the fluid source to the endoscope for endoscopic lavage.

In some embodiments, a method includes a fluid source being sealed by a cap and conveying a gas from a gas source into a chamber of the fluid source to increase the pressure within the chamber. The method further includes conveying a first volume of fluid out of the chamber in response to the increase of pressure. The first volume of fluid is conveyed at a first flow rate via a first tube to an endoscope for endoscopic lens cleaning. The method includes conveying a second volume of fluid out of the chamber. The second volume of fluid is conveyed at a second flow rate, substantially greater than the first flow rate, via a second tube to an endoscope for endoscopic irrigation. Furthermore, the gas is conveyed from the gas source into the chamber of the fluid source at a rate sufficient to offset a change in pressure produced by the conveyance of at least a portion of the first volume of fluid or the second volume of fluid. In some embodiments, the first volume of the fluid can be conveyed during a first time period and the second volume of the fluid can be conveyed during a second time period. The first and second time period can be, for example, at least partially concurrent (i.e., occurring at the same time) or independent.

FIG. 1 is an illustration of an example of a conventional endoscopic system. An endoscope 60 is connected to an endoscopic control unit 3 that supplies both the light from the light source 3*b* and air from the air pump 3*a* to the endoscope 60. Air travels from the air pump 3*a* through a connector 5 to an air tube 3*c*, pressurizing a fluid source 6 and forcing the fluid out of a lens cleaning tube 2a at a low flow rate. When the pressure begins to drop in the fluid source 6, the endoscopic control unit 3 replenishes the diminished air supply. The endoscopist can choose to clean the lens (not illustrated) of an endoscope by fully depressing the control button 61a when desired, thereby allowing fluid to flow to clean the lens. In some embodiments, a filter (not illustrated) is disposed at a location between the air pump 3a and the endoscope 60 to prevent airborne infectious materials from passing into/through the endoscope.

As discussed above, a high flow rate is typically required for endoscopic lavage (irrigation) where the primary function is to keep the operative field clean from debris (e.g., —stool, bleeding). This function is traditionally accomplished with the use of a peristaltic pump 4. Lavage tubing 4c is inserted into the peristaltic pump head 4a and fluid is expelled by depressing a footswitch (not shown) when fluid is required. To prevent a negative pressure from forming in the fluid source 1 and the lavage tubing 4c, an air vent (not shown) is included in the cap 1a of fluid source 1. This vent feature allows room air to flow into the fluid source 1, which equalizes the pressure and prevents negative pressure. If a negative pressure were to develop, the potential for infection is increased because infectious matter could flow back from the patient toward the fluid source 1. In some embodiments, a filter can be placed in fluid communication with the vent to prevent infectious material from entering the fluid source.

Figure 2:
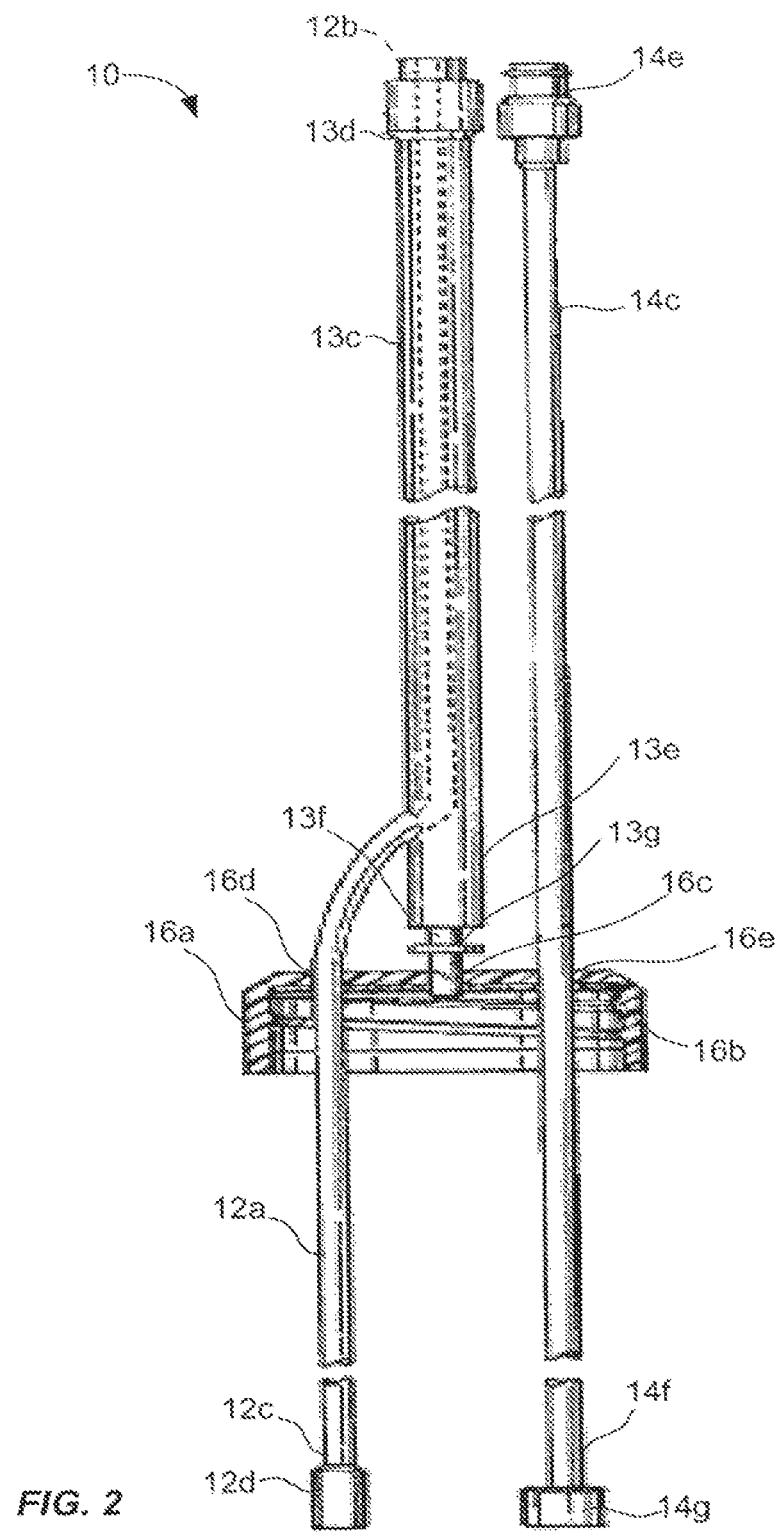
FIG. 2 is a cross-sectional side view of a hybrid apparatus, according to an embodiment.
Figure 3:
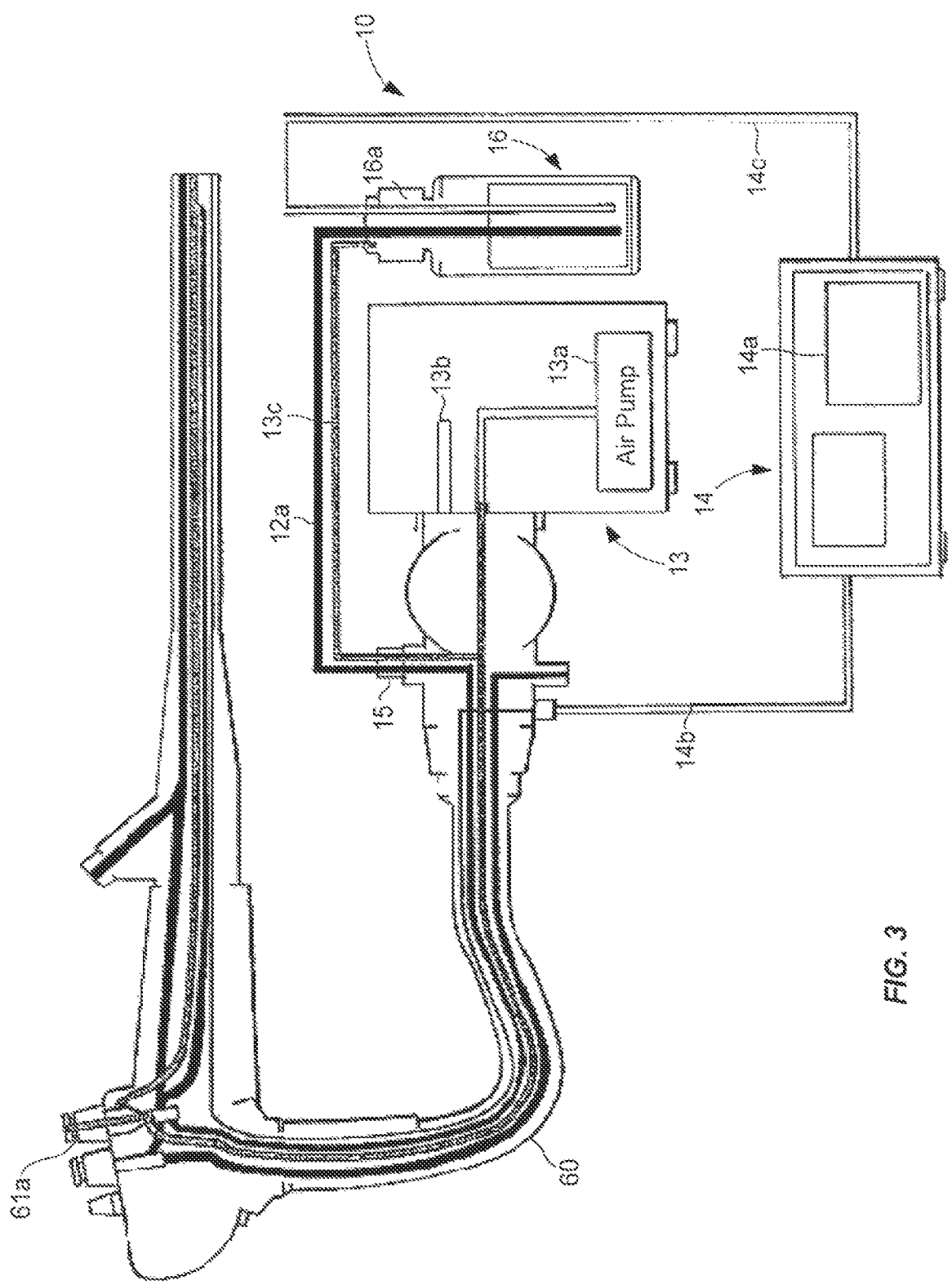
FIG. 3 is a cross-sectional schematic illustration of a hybrid apparatus used in an endoscopic system, according to the embodiment of FIG. 2.

FIGS. 2 and 3 illustrate an embodiment of a hybrid apparatus 10 where the supply conduits for endoscopic lavage (irrigation) and lens cleaning are connected to and draw fluid from a single fluid source 16. The hybrid apparatus 10 includes a cap 16a, an air supply tube 13c, a lens cleaning tube 12a, and a lavage tube 14c, as shown in FIG. 2. The cap 16a is configured to couple to a fluid source 16 (FIG. 3) in any suitable arrangement as dictated by the fluid source. For example, in some embodiments the cap 16a can include a series of threads configured to mate with a series of threads on a receiving portion of the fluid source 16. In some embodiments, the cap 16a includes a protrusion and/or series of protrusions to create a snap fit with a receiving portion of the fluid source 16. As shown in FIG. 2, the cap 16a includes a membrane 16b, a first opening 16c, a second opening 16d, and a third opening 16e. The membrane 16b engages the fluid source 16 to provide a fluid-tight seal and can be any suitable sealing mechanism. For example, the membrane can be an o-ring, flange, collar, and/or the like and can be formed of any suitable material.

The air supply tube 13c includes a first end 13d and a second end 13e and defines a lumen therebetween. The air supply tube 13c can provide an air supply from an air pump 13a (FIG. 3) to the fluid source 16. More specifically, the first end 13d of the air supply tube 13c couples to an endoscopic control unit 13 via a connector 15, as shown in FIG. 3. The endoscopic control unit includes the air pump 13a, a light source 13b, and any other suitable mechanism for endoscopic procedures. The first end 13d of the air supply tube 13c can couple to the endoscopic control unit in any suitable manner as dictated by the control unit (i.e., the first end 13d can be coupled to any suitable fitting configured to couple to a specific endoscopic control unit such as, for example, Fujinon, Olympus, or Pentax). In some embodiments, an air filter (not illustrated) can be disposed between the air pump 13a and fluid source 16. In other embodiments, the air filter can be coupled directly to the air pump 13a.

The second end 13e of the air supply tube 13c is configured to receive a fitting and/or connector 13f. The fitting 13f is configured to couple the second end 13e of the air supply tube 13c to the cap 16a, as shown in FIG. 2. More specifically, the fitting 13f can be inserted into the second end 13e of the air supply tube and create a friction fit. Similarly, the fitting 13f can be inserted into the first opening 16c of the cap 16a. A one-way check valve 13g can be disposed in the fitting 13f to prevent backflow into the air supply tube 13c. In some embodiments, a second one-way check valve can be disposed within the fitting of the first end 13d. In this manner, the air supply tube 13c is configured to supply air to the fluid source 16 and prevent the back flow of air into the air supply tube 13c. Therefore, in use, the pressure builds within fluid source 16, and a pressure differential between the fluid source and air supply tube 13c can form. The pressure differential helps maintain a positive pressure in the fluid source 16 even when large volumes of fluid are removed from the fluid source 16 during high flow rate lavage (irrigation). Said another way, the valve 13g can prevent a negative pressure from forming in the fluid source due to the time delay of air being delivered from the air pump 13a through the air supply tube 13c when a large volume of fluid is removed for lavage.

As described above, the air supply tube 13c defines a lumen. The lumen of the air supply tube 13c is configured to receive at least a portion of the lens cleaning tube 12a, shown in FIG. 2. In this manner, the lumen defined by the air supply tube 13c is sufficiently large to house the lens cleaning tube 12a as well as provide the air to the fluid source 16. The lens cleaning tube 12a is configured to exit the lumen defined by the air supply tube 13c in any suitable air-tight manner, such as, for example, an aperture, fitting, collar, and/or the like. The lens cleaning tube 12a includes a first end 12b and a second end 12c and defines a lumen therebetween. The lens cleaning tube 12a is configured to transport the fluid from the fluid source 16 to the endoscope for endoscopic lens cleaning. Similar to the first end 13d of the air supply tube 13c, the first end 12b of the lens cleaning tube 12a couples to the endoscopic control unit 13 via the connector 15, as shown in FIG. 3.

A portion of the lens cleaning tube 12a is configured to be disposed within the fluid source 16. More specifically, the second opening 16d defined by the cap 16a receives a portion of the lens cleaning tube 12a. The second end 12c of the lens cleaning tube 12a is configured to be disposed within the fluid contained in the fluid source 16. Additionally, the second end 12c includes a one-way check valve 12d at the end disposed in the fluid of the fluid source 16. In this manner, the valve 12d allows fluid to travel out of the fluid source 16 through the lens cleaning tube 12a and prevents fluid from being sucked out of the lens cleaning tube 12a if a negative pressure forms in the fluid supply when, for example, high fluid flow rate lavage (irrigation) is called for by the endoscopist.

The lavage tube 14c includes a first end 14e and a second end 14f and defines a lumen therebetween. The lavage tube 14c can transport the fluid from the fluid source 16 to the peristaltic pump 14. As shown in FIG. 3, a second lavage tube 14b can be used to provide the fluid from the peristaltic pump to the endoscopic control unit 13, specifically endoscope 60. The first end 14e of the lavage tube 14c is configured to couple to the peristaltic pump 14 in any suitable manner as dictated by the specific peristaltic pump (i.e., a specific fitting, collar, or coupling). Furthermore, the first end 14e of the lavage tube 14c includes a one-way check valve configured to allow fluid to flow out of the fluid source 16 through the lavage tube 14c and prevents any backflow of fluid from the peristaltic pump 14 from entering the lavage tube 14c. The third opening 16e (FIG. 2) defined by the cap 16a is configured to receive a portion of the lavage tube 14c. The second end 14f of the lavage tube 14c is disposed within the fluid contained in the fluid source 16. The second end 14f of the lavage tube 14c includes a weight 14g configured to maintain the second end 14f of the lavage tube 14c in the fluid contained in the fluid source 16.

During operation, the valve 12d of the lens cleaning tube 12a and the valve 13g of the air supply tube 13c allow for multiple different pressures to be maintained in the system. For example, an endoscopist can depress a footswitch (not shown) to activate a flow of the fluid for endoscopic lavage and/or depress the control button 61a to activate a flow of the fluid for endoscopic lens cleaning. As fluid is removed from the fluid source 16 either via the lens cleaning tube 12a or via the lavage tube 14c, the pressure in the fluid source 16 can drop to a second pressure, lower than the original pressure, which can be the same as the pressure in the air supply tube 13c. Even though pressure in the fluid source 16 has changed, the valve 13g is configured to maintain the pressure in the lens cleaning tube 12a at substantially its original pressure. Thus, the lens cleaning function can be used since the original pressure is still present in tube 12a. When the pressure is reduced in the fluid source 16 by use of either the optical viewing lens cleaning function, the high flow rate lavage (irrigation) function, or both functions simultaneously, the reduced pressure is compensated for by the air pump 13a via the air supply tube 12b. This combination of tubing and valves provides for the safe simultaneous use of endoscopic lavage (irrigation) and optical viewing lens cleaning from a single fluid source.

Figure 4:
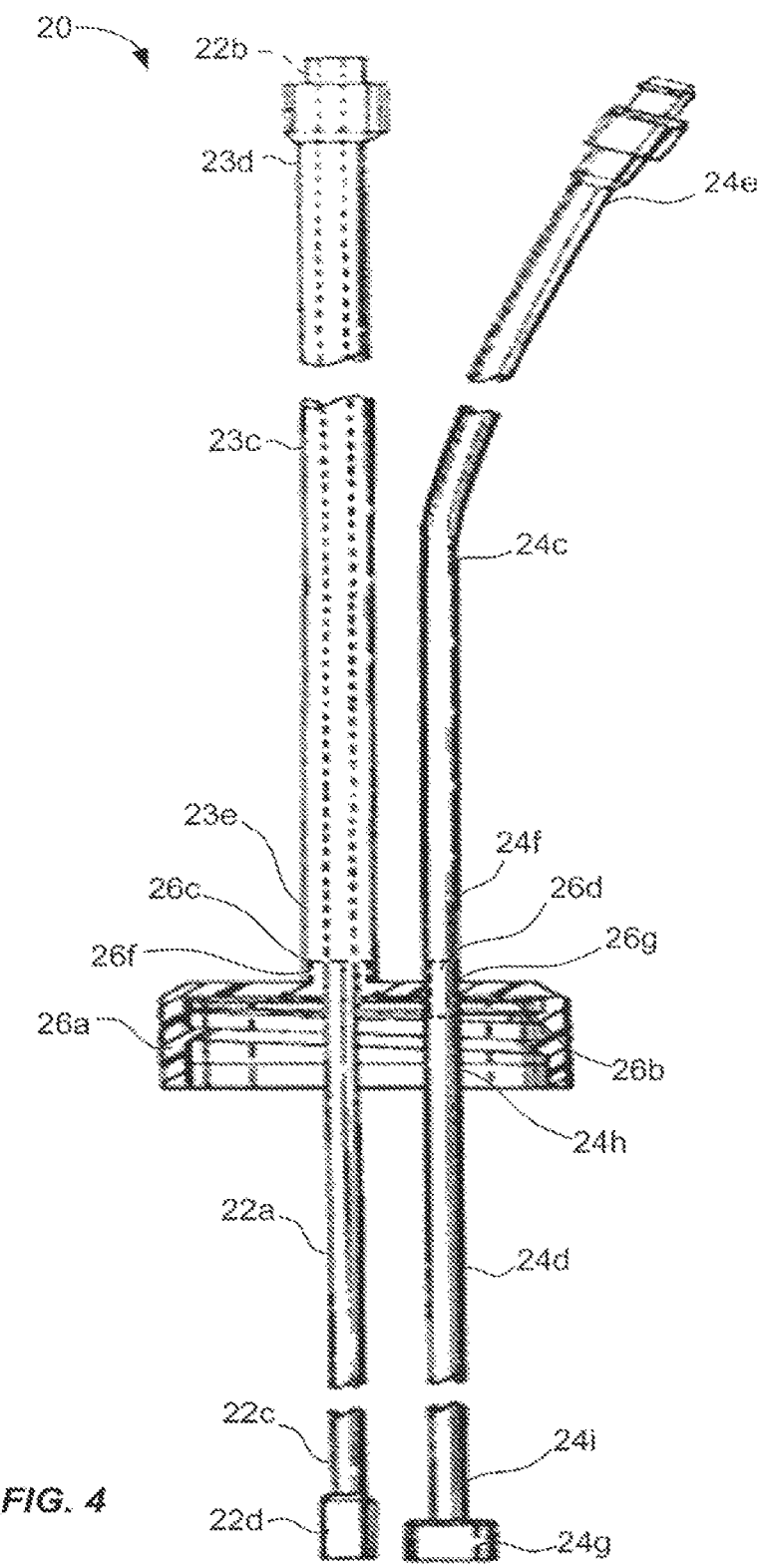
FIG. 4 is a cross-sectional side view of a hybrid apparatus, according to an embodiment.
Figure 5:
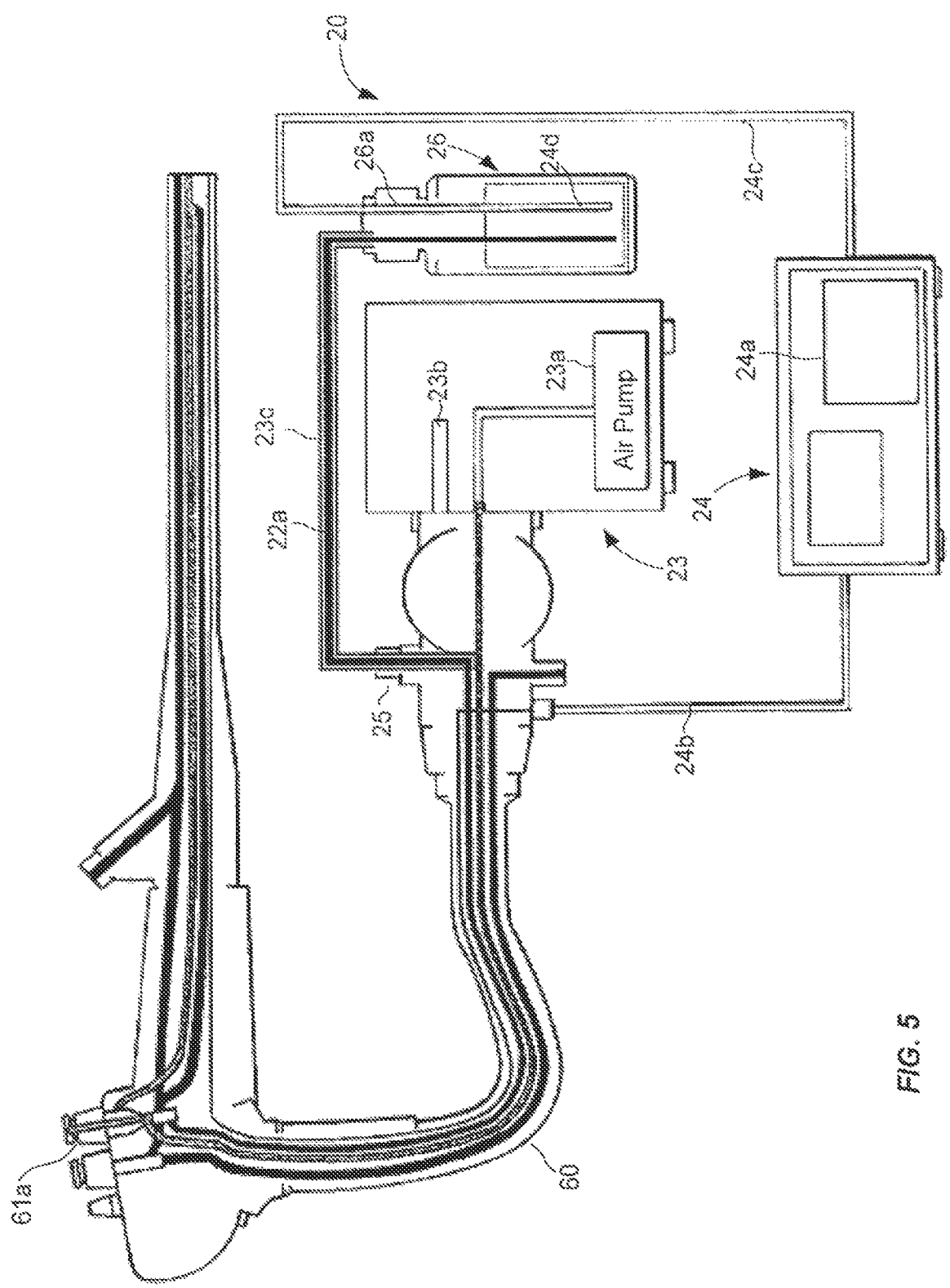
FIG. 5 is a cross-sectional schematic illustration of the hybrid apparatus used in an endoscopic system, according to the embodiment of FIG. 4.

FIGS. 4 and 5 illustrate an embodiment of a hybrid apparatus 20 where the supply conduits for endoscopic lavage (irrigation) and lens cleaning are connected to and draw fluid from a single fluid source. The hybrid apparatus 20 includes a cap 26a, an air supply tube 23c, a lens cleaning tube 22a, and a lavage tube 24c, as shown in FIG. 4. The cap 26a is configured to couple to a fluid source 26 (FIG. 5) in any suitable arrangement as dictated by the fluid source. For example, in some embodiments the cap 26a can include a series of threads configured to mate with a series of threads on a receiving portion of the fluid source 26. In some embodiments, the cap 26a includes a protrusion and/or series of protrusions to create a snap fit with a receiving portion of the fluid source 26. As shown in FIG. 4, the cap 26a includes a membrane 26b, a first opening 26c, and a second opening 26d. The membrane 26b engages the fluid source to provide an air/fluid-tight seal and can be any suitable sealing mechanism, for example those described with respect to FIG. 2.

The air supply tube 23c includes a first end 23d and a second end 23e and defines a lumen therebetween. The air supply tube 23c can provide an air supply from an air pump 23a (FIG. 5) to the fluid source 26. More specifically, the first end 23d of the air supply tube 23c couples to an endoscopic control unit 23 via a connector 25, as shown in FIG. 5. The first end 23d of the air supply tube 23c is similar in form and function to the first end 13d of the air supply tube 13c described with respect to FIGS. 2 and 3, and, therefore, is not described in detail herein. The air supply tube 23c is configured to receive at least a portion of the lens cleaning tube 22a, shown in FIG. 4. In this manner, the lumen defined by the air supply tube 23c is sufficiently large to house the lens cleaning tube 22a as well as provide the air to the fluid source 26. Similarly stated, the coaxial configuration creates an annular space in which the air can be delivered from the air pump 23a to the fluid source 26. As discussed above, an air filter (not illustrated) can be disposed between the air pump 23a and the fluid source 26. The lens cleaning tube 22a is configured to exit the lumen defined by the air supply tube 23c via an opening defined by the second end 23e of the air supply tube 23c. The second end 23e of the air supply tube 23c is configured to receive a fitting 26f that defines a first opening 26c. The fitting 26f is, for example, unitarily formed with the cap 26a and extends from a top surface of the cap 26a. The fitting 26f is configured to couple the second end 23e of the air supply tube 23c to the cap 26a, as shown in FIG. 4. More specifically, the second end 23e of the air supply tube 23c can be inserted over the fitting 26f and create a friction fit. The first opening 26c defined by the fitting 26f is configured to receive at least a portion of the lens cleaning tube 22a therethrough. The fitting 26f is configured such that the first opening 26c is of a large enough diameter to receive the lens cleaning tube 22a and allow sufficient air to enter and/or exit the fluid supply 16 (see FIG. 3) as an endoscopist may require.

In some embodiments, a one-way check valve can be disposed within the fitting of the first end 23d. In this manner, the air supply tube 23c is configured to supply air to the fluid source 26 and prevent the back flow of air. Therefore, in use, the pressure builds within fluid source 26, and a pressure differential between the fluid source and air supply tube 23c can form. The pressure differential helps maintain a positive pressure in the fluid source 26 even when large volumes of fluid are removed from the fluid source 26 during high flow rate lavage (irrigation).

As described above, the lens cleaning tube 22a is at least partially disposed within the lumen defined by the air supply tube 23c. The lens cleaning tube 22a includes a first end 22b and a second end 22c and defines a lumen therebetween. The lens cleaning tube 22a is configured to transport the fluid from the fluid source 26 to the endoscope for endoscopic lens cleaning. Similar to the first end 23d of the air supply tube 23c, the first end 22b of the lens cleaning tube 22a couples to the endoscopic control unit 23 via the connector 25, as shown in FIG. 5. A portion of the lens cleaning tube 22a is configured to pass through the first opening 26c defined by the fitting 26f and be disposed within the fluid source 26. The second end 22c of the lens cleaning tube 22a is similar in form and function to the second 12c of the lens cleaning tube 12a described with respect to FIGS. 2 and 3, and, therefore, is not described in detail herein.

The lavage tube 24c includes a first end 24e and a second end 24f and defines a lumen therebetween. The lavage tube 24c can transport the fluid from the fluid source 26 to the peristaltic pump 24. As shown in FIG. 5, a second lavage tube 24b can be used to provide the fluid from the peristaltic pump to the endoscopic control unit 23. The first end 24e of the lavage tube 24c is configured to couple to the peristaltic pump 24 in any suitable manner as dictated by the specific peristaltic pump (i.e., a specific fitting, collar, or coupling). Furthermore, the first end 24e of the lavage tube 24c includes a one-way check valve configured to allow fluid to flow out of the fluid source 26 through the lavage tube 24c and prevents any backflow of fluid from the peristaltic pump 24 from entering the lavage tube 24c. The cap 26a includes a fitting 26g configured to receive at least a portion of the lavage tube 24c. More specifically, the fitting 26g is unitarily formed with the cap 26a such that a portion of the fitting 26g extends away from the top surface of the cap 26a in a similar direction as that of the fitting 26f. Conversely, a second portion of the fitting 26g extends away from the top surface of the cap 26a in a substantially opposite direction. Similarly stated, the fitting 26g is configured to extend above and below the top surface of the cap 26a and defines a second opening 26d therebetween. The second end 24f of the lavage tube 24c is configured to be inserted over the fitting 26g and create a friction fit.

A third lavage tube 24d can be disposed within the fluid contained in the fluid source 26. A first end 24h of the third lavage tube 24d is configured to be inserted over the second portion of the fitting 26g, thereby creating a friction fit. The second end 24i of the lavage tube 24d includes a weight 24g configured to maintain the second end 24f of the lavage tube 24c in the fluid contained in the fluid source.

During operation, the valve 22d of the lens cleaning tube 22a and the air supply tube 23c allow for multiple different pressures to be maintained in the system. For example, an endoscopist can depress a footswitch (not shown) to activate a flow of the fluid for endoscopic lavage and/or depress the control button 61a to activate a flow of the fluid for endoscopic lens cleaning. As fluid is removed from the fluid source 26 either via the lens cleaning tube 22a or via the lavage tube 24c, the pressure in the fluid source 26 can drop to a second pressure, lower than the original pressure, which can be the same as the pressure in the air supply tube 23c. Even though pressure in the fluid source 26 has changed, the air supply tube 23c is configured to maintain the pressure in the lens cleaning tube 22a at substantially its original pressure. Thus, the lens cleaning function can be used since the original pressure is still present in tube 22a. When the pressure is reduced in the fluid source 26 by use of either the optical viewing lens cleaning function, the high flow rate lavage (irrigation) function, or both functions simultaneously, the reduced pressure is compensated for by the air pump 23a via the air supply tube 22b. This combination of tubing and valves provides for the simultaneous use of endoscopic lavage and optical viewing lens cleaning from a single fluid source.

Figure 6:
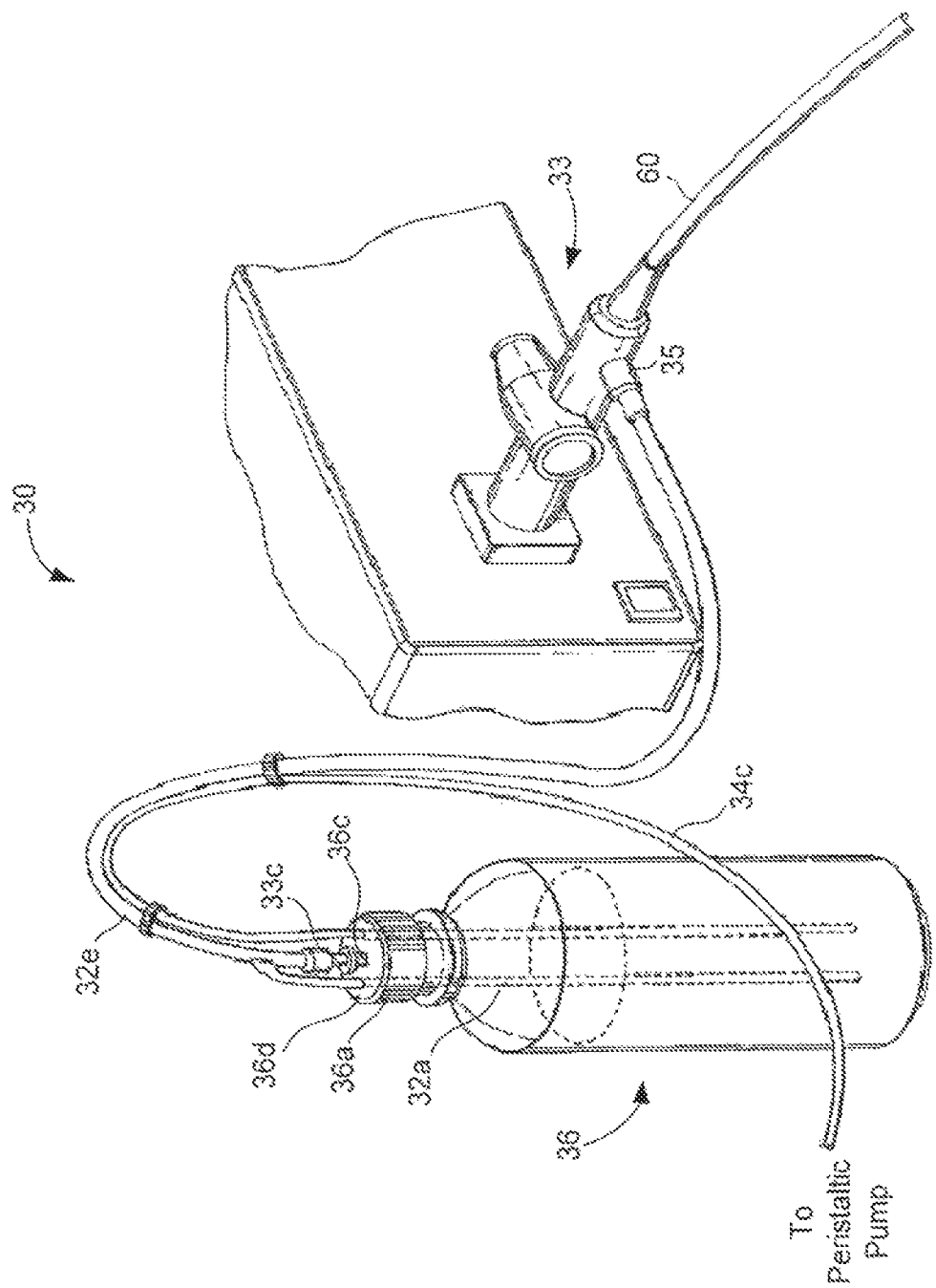
FIG. 6 is a perspective view of a portion of a hybrid apparatus, according to an embodiment.

As shown in FIG. 6, a fluid source 36 is in direct fluidic communication with the endoscope 60 via a tube 32e, which houses both a lens cleaning tube 32a and an air supply tube 33c. In some embodiments, the tube 32e is a multi-lumen tube. At one end, the tube 32e terminates at a connector 35. The connector 35 is configured to be coupled to both the air and water connections from the endoscope 60 via the tube 33c and 32a respectively and is also connected to the endoscopic control unit 33. At the opposite end of the tube 32e, the water supply tube 32a passes through the second opening 36d in a cap 36a and extends down towards the bottom (or substantially close to the bottom) of the fluid source 36, while the air supply tube 33c terminates at the first opening 36c of the cap 36a (or extends slightly past the cap 36a) to supply air to the fluid source 36. The lavage tube 34c can be separate from or attached to the tube 32c and is connected to the peristaltic pump (not shown in FIG. 6). In some embodiments, the tubes 34c and 32e are a unitary construction multi-lumen tube. The lavage tube 34c also passes through the cap 36a and extends down towards the bottom (or substantially close to the bottom) of the fluid source 36.

Figure 7:
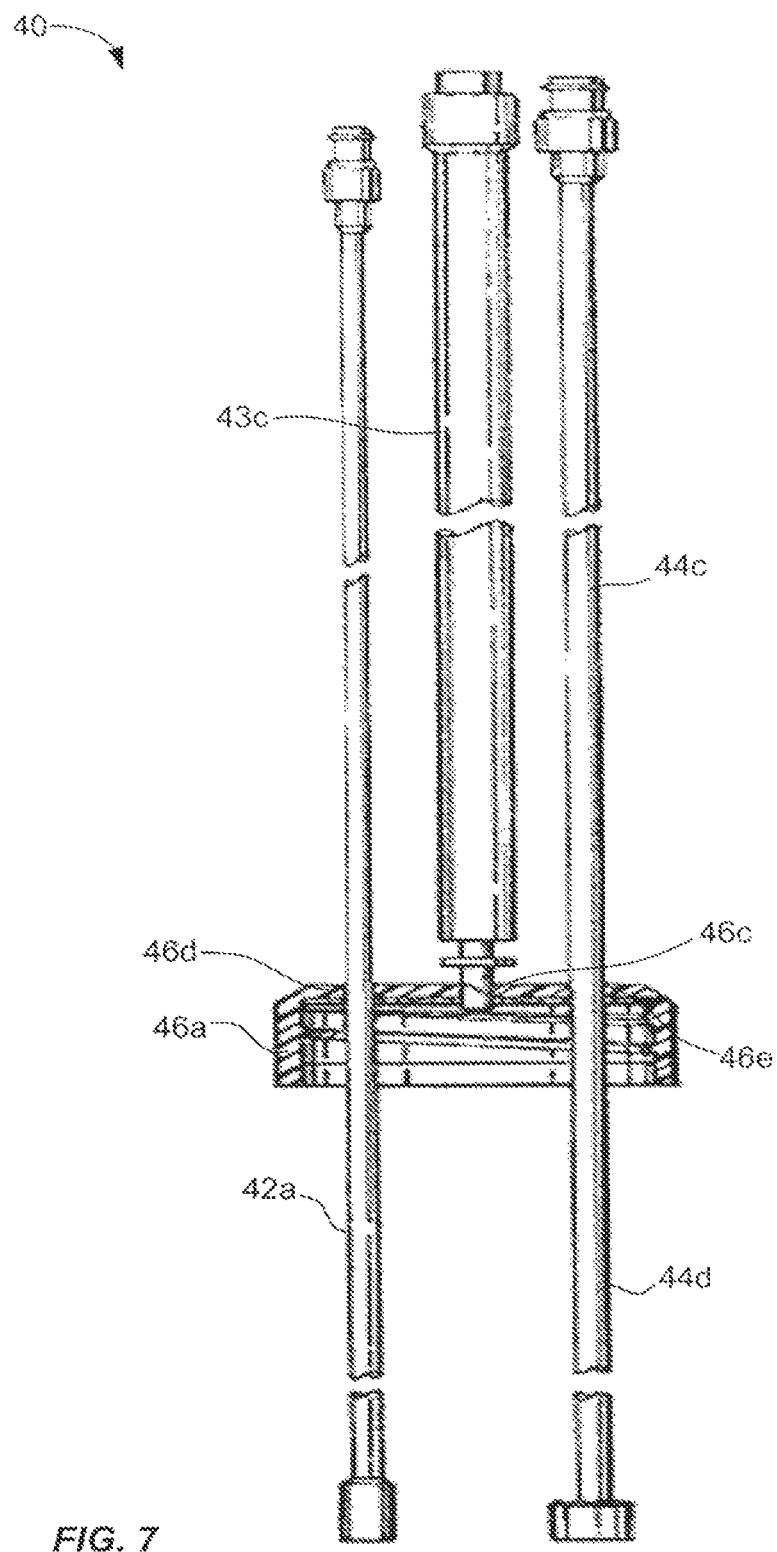
FIG. 7 is a cross-sectional side view of a hybrid apparatus, according to an embodiment.

In some endoscopic systems, an endoscope, a peristaltic pump, and/or an endoscopic control unit (including the air pump) can be in such an arrangement as to require the tubes in different configurations. For example as shown in FIG. 7, a hybrid apparatus 40 includes a cap 46a, an air supply tube 43c, a lens cleaning tube 42a, and a lavage tube 44c. Similar to the cap 16a as described with respect to FIG. 2, the cap 46a includes a first opening 46c, a second opening 46d, and a third opening 46e configured to receive at least a portion of the air supply tube 43c, the lens cleaning tube 42a, and the lavage tube 44c, respectively. The interactions of the cap 46a, the fluid source (not shown in FIG. 7), and the supply conduits are substantially similar to the interactions of the cap, the fluid source, and the supply conduits of the hybrid apparatus 10 described with respect to FIG. 2, thus some of the features of the cap 46a, the air supply tube 43c, the lens cleaning tube 42a, and the lavage tube 44c are not described herein. In contrast to the hybrid apparatus 10 described with respect to FIG. 2, the air supply tube 43c and the lens cleaning tube 42a are not configured to be coaxial. Similarly stated, the arrangement of the endoscope, the peristaltic pump, and the endoscopic control unit can require the supply conduits to be in a non-coaxial configuration. In this manner, the lens cleaning tube 42a is not disposed within any portion of the air supply tube 43c. Therefore, the lens cleaning tube 42a, the air supply tube 43c, and the lavage tube 44c can be independently configured and, as such, can include any suitable valve, fitting, collar, or connector for coupling to the receiving port of the respective device.

Figures 8A, 8B:
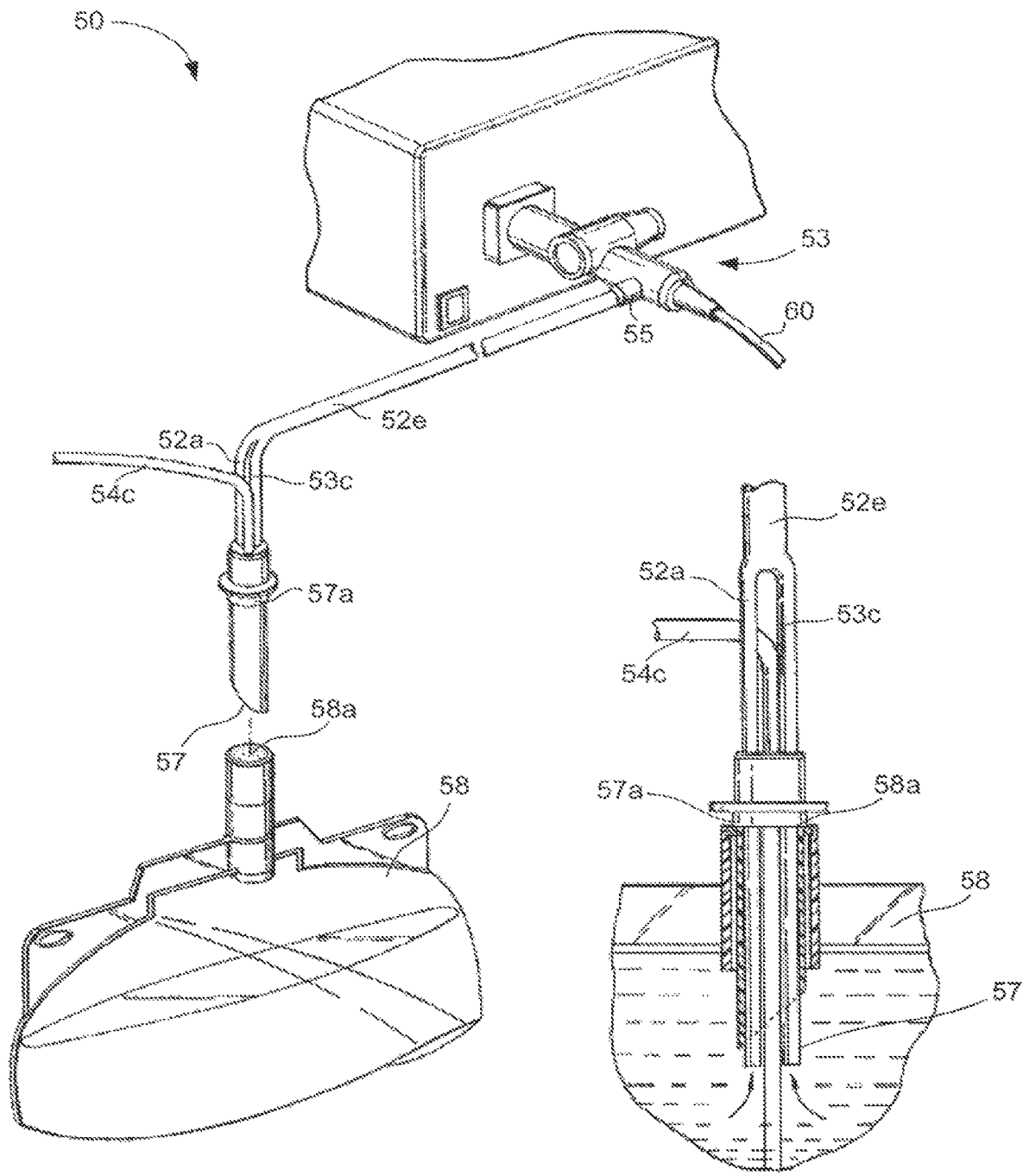
FIG. 8A is a perspective view of a hybrid apparatus, according to an embodiment.
FIG. 8B is a magnified cross-sectional view of a portion of the hybrid apparatus, according to the embodiment of FIG. 8A.

FIGS. 8A and 8B illustrate an embodiment of a hybrid apparatus 50 where the supply conduits for endoscopic lavage (irrigation) and lens cleaning are connected to and draw fluid from a single fluid source 58. The hybrid apparatus 50 includes an air supply tube 53c, a lens cleaning tube 52a, and a lavage tube 54c. Portions of the air supply tube 53c, the lens cleaning tube 52a, and the lavage tube 54c can be substantially similar to portions of the air supply tube 33c, the lens cleaning tube 32a, and the lavage tube 34c. Thus, some features of the hybrid apparatus 50 will not be described in detail with reference to FIGS. 8A and 8B.

In some embodiments, the air supply tube 53c and the lens cleaning tube 52a can be at least partially disposed in a multi-lumen tube 52e. At one end, the tube 52e terminates at a connector 55. In some embodiments, the other end the multi-lumen tube 52e splits, branching into the air supply tube 53c and the lens cleaning tube 52a. The hybrid apparatus 50 includes a fluid spike 57 that is configured to couple to the air supply tube 53c, the lens cleaning tube 52a, and the lavage tube 54c. The fluid spike is configured to pierce a septum port 58a included in a flexible fluid source 58. The fluid spike 57 can be formed of any suitable material capable of piercing the septum port 58a. The fluid spike 57 can include a sealing member 57a configured to engage the septum port 58a and provide a fluid tight seal. In some embodiments, the fluid spike 57 can include a locking mechanism and/or protrusion capable of selectively engaging at least a portion of the septum port 58a and/or fluid source 58 and securing the fluid spike 57 to the fluid source 58.

The air supply tube 53c is configured to terminate at the fluid spike 57 and provide air to the fluid source 58, thereby regulating the pressure therein. The lens cleaning tube 52a and the lavage tube 54c are configured to extend through the fluid spike 57 and be disposed within the fluid contained in the fluid source 58. Although not shown, the hybrid apparatus 50 can include valves similar to those described above. In this manner, the hybrid apparatus 50 can function similarly to the hybrid apparatuses described herein. For example, the hybrid apparatus 50 can transport a portion of a fluid to the endoscope for endoscopic lens cleaning via the lens cleaning tube 52a in response to an increase of pressure within the fluid supply 58. Similarly, the hybrid apparatus 50 can transport a portion of the fluid to the endoscope for endoscopic lavage via the lavage tube 54c in response to a peristaltic pump (not shown).

Figure 9:
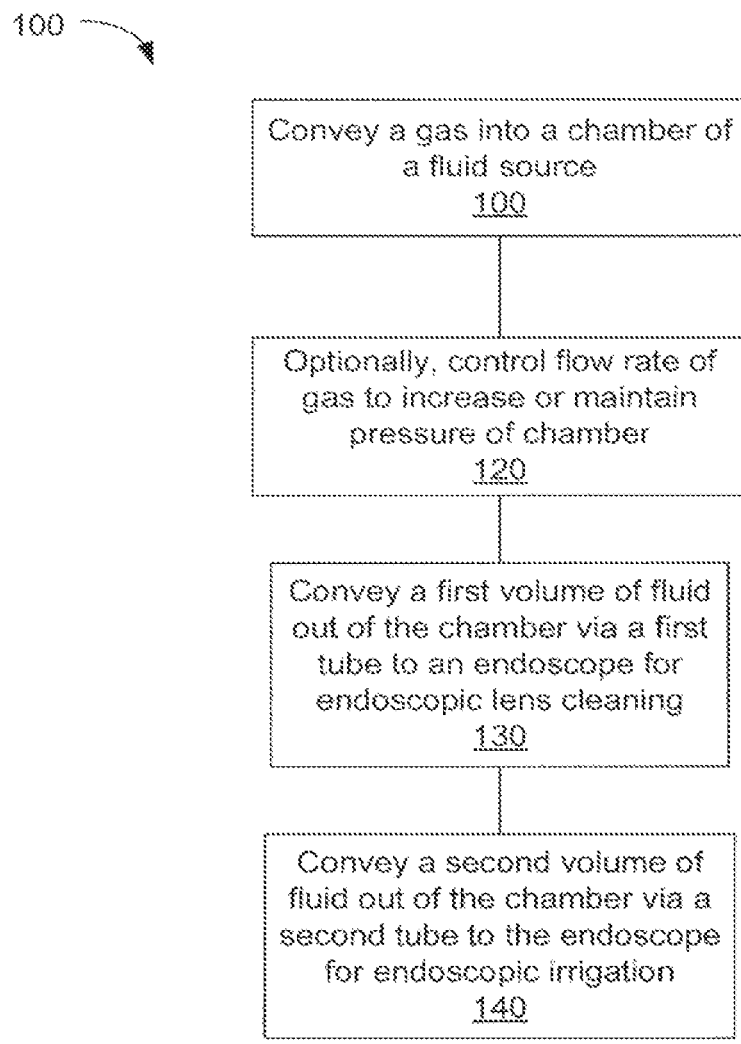
FIG. 9 is a flow chart illustrating a method of using a hybrid apparatus for fluid supply for endoscopic irrigation and lens cleaning.

FIG. 9 is a flow chart illustrating a method 100 of using a hybrid apparatus for fluid supply for endoscopic irrigation and lens cleaning. The method 100 can be implemented by any hybrid apparatus included in an endoscopic system, as described herein. The method 100 includes conveying a gas (e.g., atmospheric air, oxygen, $CO_2$, and/or the like) from a gas source to a chamber of a fluid source at 110. The fluid source can be any suitable fluid source described herein, such as, for example, a flexible or rigid container. The gas can be conveyed to the chamber of the fluid source in such a manner as to control (i.e., increase or maintain) the pressure within the chamber at 120. In some embodiments, the flow of the gas into the chamber is controlled by a valve included in an air supply tube, such as, for example, the air supply tube 13c described with respect to FIG. 2. In other embodiments, an air pump can include the valve. In such embodiments, the air pump prevents the backflow of air from the chamber through the pump.

The method 100 further includes conveying a first volume of fluid out of the chamber via a first tube to an endoscope for endoscopic lens cleaning at 130. The first tube can be any suitable tube described herein, for example, the air tube 23c described with respect to FIG. 4. In some embodiments, the first volume of fluid can be conveyed in response to the increase of pressure in the chamber of the fluid source. The first volume of fluid can be conveyed at a first flow rate suitable for endoscopic lens cleaning. In some embodiments, the first tube includes a valve. In this manner, the air supply tube can convey a gas to the chamber of the fluid source, thereby increasing the pressure such that the valve of the first tube opens to convey the first volume of fluid at the first flow rate.

The method 100 also includes conveying a second volume of fluid out of the chamber via a second tube to the endoscope for endoscopic irrigation at 140. Similar to the first tube, the second tube can be any suitable tube described herein. In some embodiments, the flow of the second volume can be in response to a peristaltic pump. In this manner, the peristaltic pump can convey the second volume of the fluid to the endoscope at a second flow rate. In some embodiments, the second flow rate is greater than the first flow rate of the first volume. The second flow rate can be any flow rate suitable for endoscopic lavage. Additionally, the gas source can convey the gas, via the air supply tube, in response to the change of pressure within the chamber of the fluid source produced by the flow of the first volume and/or the second volume.

In some embodiments, the first volume and the second volume can be conveyed in response to a manual control button included in the endoscopic system. In such embodiments, an endoscopist can depress a control button to initiate the flow of the first volume at a first time and depress a control button to initiate the flow of the second volume at a second time. The first time and the second time can be at substantially different times, the same time, or include any portion of concurrence. In some embodiments, the flow of the first volume and the second volume can be automatic. In such embodiments, an endoscope can provide a signal to an endoscopic control unit and/or peristaltic pump to convey the flow of the first volume and/or second volume.

The components of the hybrid apparatus can be packaged together or separately. For example, the cap and supply conduits can be in a package while an assortment of fittings, connectors, valves, and/or the like can be package separately. Each of the components discussed herein can be unitarily constructed or can be a combination of parts. For example, in reference to FIG. 4, the cap 26a and fittings 26f and 26g are unitarily constructed. In some embodiments, the fittings 26f and 26g can be formed independently of the cap 26a and be configured to couple to the cap 26a (e.g., as threaded inserts and/or the like). Other aspects of the apparatus shown and described can be modified to affect the performance of the apparatus. For example, the valves described herein can be configured to provide a fluid and/or gas at a given volumetric flow rate for a given endoscopic device. In some embodiments, the volumetric flow rate can vary based on the setting required by the specific brand of endoscopic device (e.g., Fujinon, Olympus, or Pentax).

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. Additionally certain events may be performed concurrently in parallel processes when possible, as well as performed sequentially. For example, while shown in the method 100 as being conveyed after the first volume, the second volume of fluid can be conveyed before the first volume or concurrently with the first volume. While various embodiments have been described as having particular features and/or combinations of components, other embodiments are possible having a combination of any features and/or components from any of embodiments as discussed above.

What is claimed is:

1. An apparatus, comprising:
   a cap configured to be coupled to a fluid source, the fluid source defining a chamber configured to contain a fluid, the cap defining a first opening, a second opening, and a third opening;
   a first tube coupled to the cap such that a lumen defined by the first tube is in fluid communication with the chamber of the fluid source via the first opening when the cap is coupled to the fluid source, the first tube configured to fluidically couple a gas source to the chamber of the fluid source;
   a second tube having a first end configured to be coupled to an endoscope and a second end configured to extend through the second opening of the cap such that, when the cap is coupled to the fluid source, a portion of the second tube is received in the chamber of the fluid source and the second end of the second tube is disposed in the fluid therein, the second tube configured to convey the fluid out of the chamber of the fluid source to the endoscope through the second tube; and
   a third tube configured to extend through the third opening of the cap such that, when the cap is coupled to the fluid source, a portion of the third tube is received in the chamber of the fluid source and an end of the third tube is disposed in the fluid therein, the third tube configured to convey the fluid out of the chamber of the fluid source to the endoscope through the third tube.

2. The apparatus of claim 1, wherein the cap includes a fitting configured to be coupled to the first tube.

3. The apparatus of claim 1, wherein the first tube is coaxial with the second tube.

4. The apparatus of claim 3, wherein a portion of the first tube forms an annular space around a portion of the second tube.

5. The apparatus of claim 1, further comprising a check valve coupleable to the second tube and, when the first end of the second tube is coupled to the endoscope, configured to prevent a flow from the endoscope to the chamber of the fluid source.

6. The apparatus of claim 5, wherein the check valve is configured to be disposed in the fluid contained by the chamber when coupled to the second tube.

7. The apparatus of claim 5, wherein the check valve is configured to be disposed proximate to the second end of the second tube.

8. The apparatus of claim 5, wherein the check valve is a first check valve and the apparatus further comprises:
a second check valve to prevent a flow from the chamber of the fluid source into the gas source.

9. The apparatus of claim 1, wherein the first tube is configured to convey the fluid from the chamber of the fluid source to the endoscope for endoscopic lens cleaning.

10. The apparatus of claim 1, wherein the cap is ventless.

11. The apparatus of claim 10, wherein the cap is configured to seal the chamber of the fluid source from atmospheric air.

12. The apparatus of claim 1, wherein the gas source is a $CO_2$ gas source.

13. The apparatus of claim 1, wherein the fluid in the chamber of the fluid source is a liquid.

14. An apparatus for delivering liquid to an endoscope, the apparatus comprising:
a first connector configured to be sealingly mated to a second connector defining a passageway and coupled to a container, the first connector defining a first opening, a second opening, and a third opening, the container defining an inner volume and configured to contain the liquid;
a first tube coupled to the first connector and configured to fluidically couple a gas source to the inner volume of the container via the first opening, the first tube having a first end and a second end and defining a lumen therebetween, the first end of the first tube configured to be coupled to the gas source;
a second tube extending through the second opening of the first connector and configured to convey the liquid contained in the inner volume of the container to the endoscope through the second tube, the second tube having a first end configured to be coupled to the endoscope and a second end configured to be disposed in the liquid contained in the inner volume of the container; and
a third tube extending through the third opening of the first connector and configured to convey the liquid contained in the inner volume of the container to the endoscope through the third tube, the third tube having a first end configured to be coupled to the endoscope and a second end configured to be disposed in the liquid contained in the inner volume of the container.

15. The apparatus of claim 14, wherein the second tube is configured to be coupled to a check valve configured to prevent the flow of liquid from the endoscope into the inner volume of the container when the first end of the second tube is coupled to the endoscope.

16. The apparatus of claim 15, wherein the check valve is configured to be disposed in the liquid contained in the inner volume of the container when coupled to the second tube.

17. The apparatus of claim 15, wherein the check valve is configured to be disposed proximate to the second end of the second tube.

18. The apparatus of claim 15, wherein the check valve is a first check valve and the apparatus further comprises:
a second check valve to prevent a flow from the inner volume of the container into the gas source.

19. The apparatus of claim 14, wherein the first tube is coaxial with the second tube.

20. The apparatus of claim 19, wherein a portion of the first tube forms an annular space around a portion of the second tube.

21. The apparatus of claim 14, wherein the first tube is configured to convey the liquid contained in the inner volume of the container to the endoscope for endoscopic lens cleaning.

22. The apparatus of claim 14, wherein the cap is ventless.

23. The apparatus of claim 14, wherein the cap is configured to seal the inner volume of the container from atmospheric air.

24. The apparatus of claim 14, wherein the gas source is a $CO_2$ gas source.

* * * * *